(12) United States Patent
Kang et al.

(10) Patent No.: US 8,475,144 B2
(45) Date of Patent: Jul. 2, 2013

(54) CHECK VALVE DIAPHRAGM MICROPUMP

(75) Inventors: Jianke Kang, Arlington, VA (US); Gregory W. Auner, Livonia, MI (US)

(73) Assignee: Wayne State University, Detroit, MI (US)

( * ) Notice: Subject to any disclaimer, the term of this patent is extended or adjusted under 35 U.S.C. 154(b) by 1008 days.

(21) Appl. No.: 12/239,919

(22) Filed: Sep. 29, 2008

(65) Prior Publication Data

US 2009/0188576 A1 Jul. 30, 2009

Related U.S. Application Data

(63) Continuation of application No. PCT/US2007/008280, filed on Mar. 30, 2007.

(60) Provisional application No. 60/787,332, filed on Mar. 30, 2006.

(51) Int. Cl.
*F04B 17/00* (2006.01)

(52) U.S. Cl.
USPC ................................. 417/413.2; 417/413.1

(58) Field of Classification Search
USPC ................................. 417/413.1, 413.2, 413.3
See application file for complete search history.

(56) References Cited

U.S. PATENT DOCUMENTS

| | | | | |
|---|---|---|---|---|
| 5,085,562 A | * | 2/1992 | van Lintel | 417/413.3 |
| 5,317,452 A | * | 5/1994 | Prentiss et al. | 359/819 |
| 5,529,279 A | * | 6/1996 | Beatty et al. | 251/11 |
| 5,529,465 A | * | 6/1996 | Zengerle et al. | 417/413.2 |
| 6,395,638 B1 | * | 5/2002 | Linnemann et al. | 438/706 |
| 6,682,318 B2 | * | 1/2004 | Takeuchi et al. | 417/322 |
| 7,258,533 B2 | * | 8/2007 | Tanner et al. | 417/413.2 |
| 2002/0098097 A1 | * | 7/2002 | Singh | 417/413.1 |
| 2004/0245605 A1 | * | 12/2004 | MacNamara et al. | 257/620 |

FOREIGN PATENT DOCUMENTS

| | | |
|---|---|---|
| EP | 0465229 | 1/1992 |
| EP | 0465229 A1 | 1/1992 |
| WO | 9701055 | 1/1997 |
| WO | 9701055 A | 1/1997 |

OTHER PUBLICATIONS

PCT/US2007/008280 International Search Report.

* cited by examiner

*Primary Examiner* — Peter J Bertheaud
*Assistant Examiner* — Dnyanesh Kasture
(74) *Attorney, Agent, or Firm* — Brinks Hofer Gilson & Lione

(57) ABSTRACT

A micropump device including a first wafer and a second wafer attached to the first wafer. The first and second wafers are configured to define a chamber therebetween having a predetermined volume. A third wafer is attached to the second wafer to define an inlet section and an outlet section in fluid communication with the chamber. At least one of the second and third wafers are formed to define a moveable diaphragm configured to change the predetermined volume of the chamber for pumping a fluid between the inlet section and the outlet section.

14 Claims, 18 Drawing Sheets

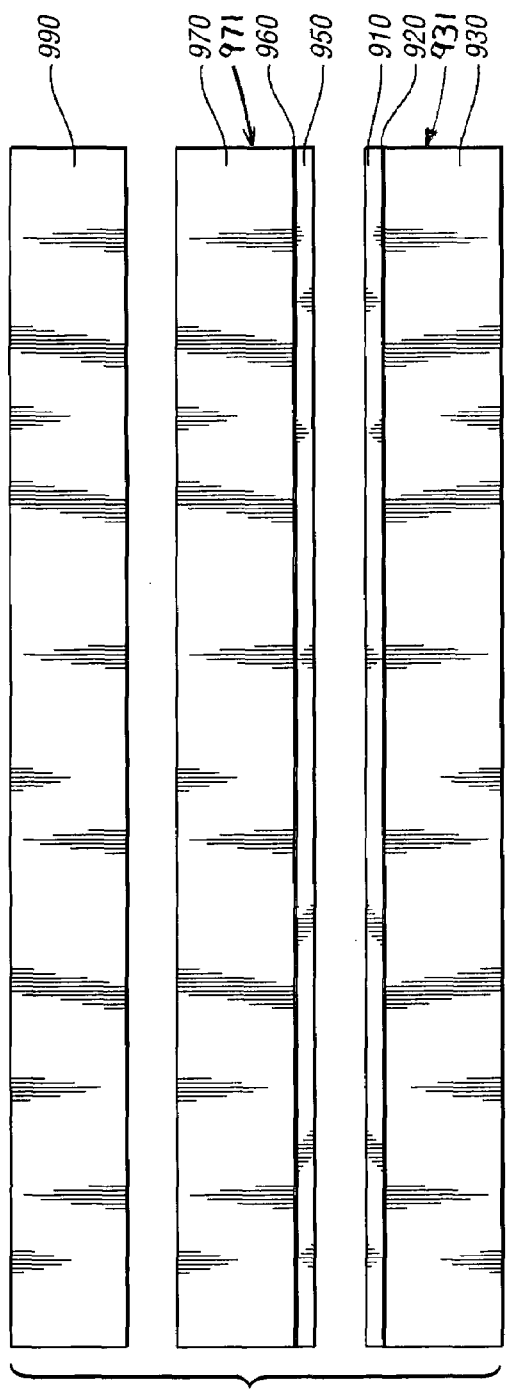
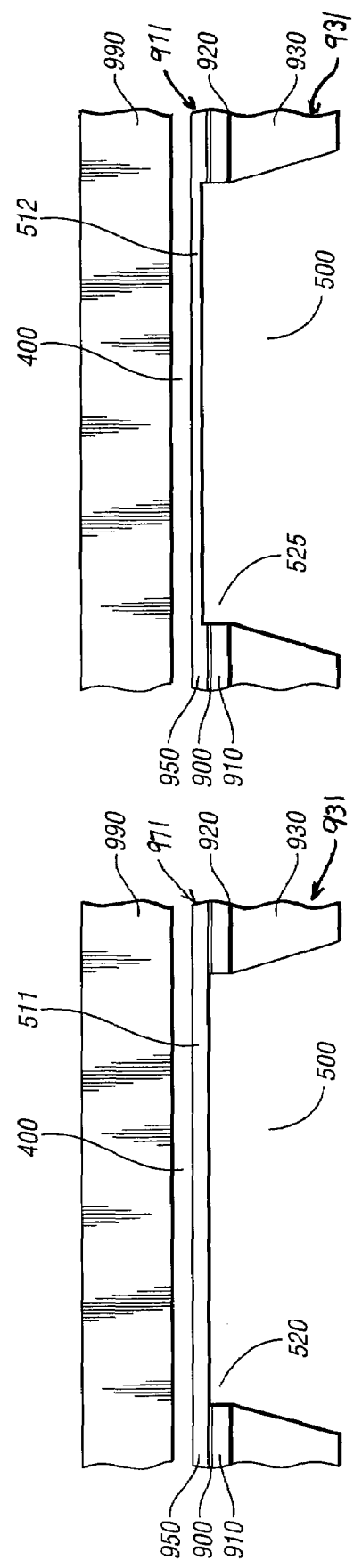

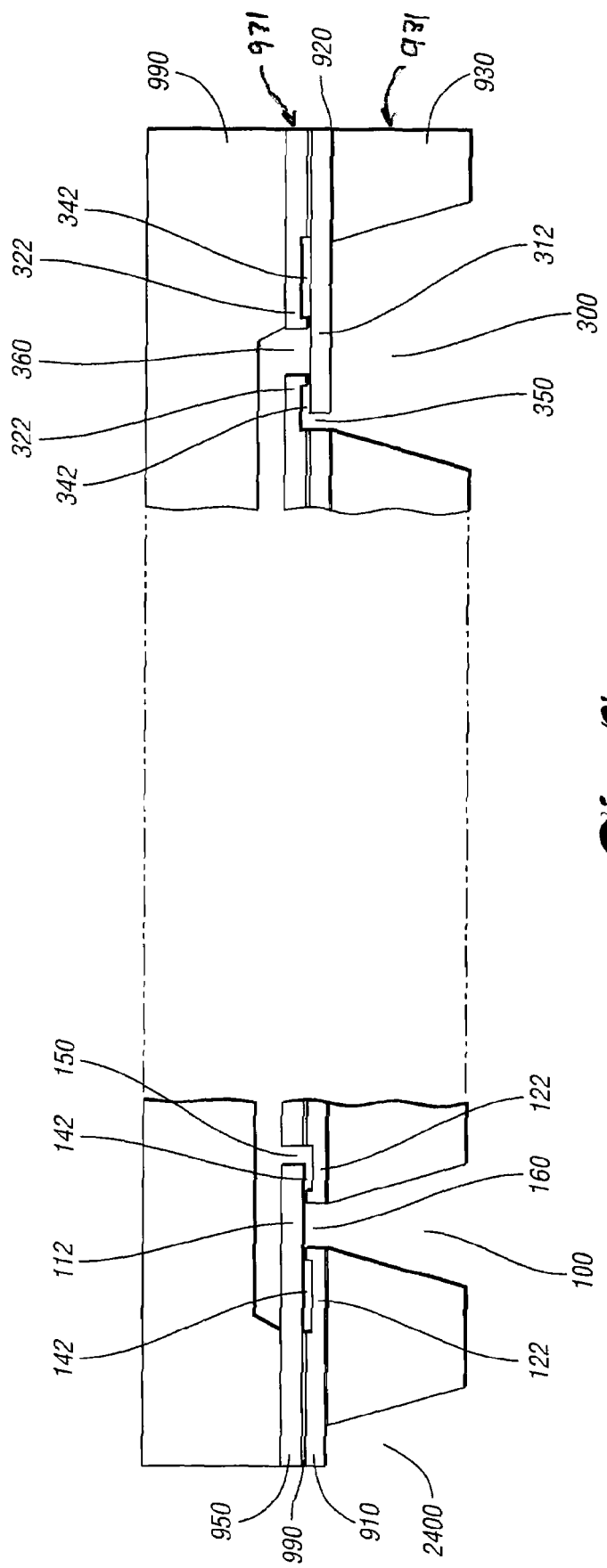

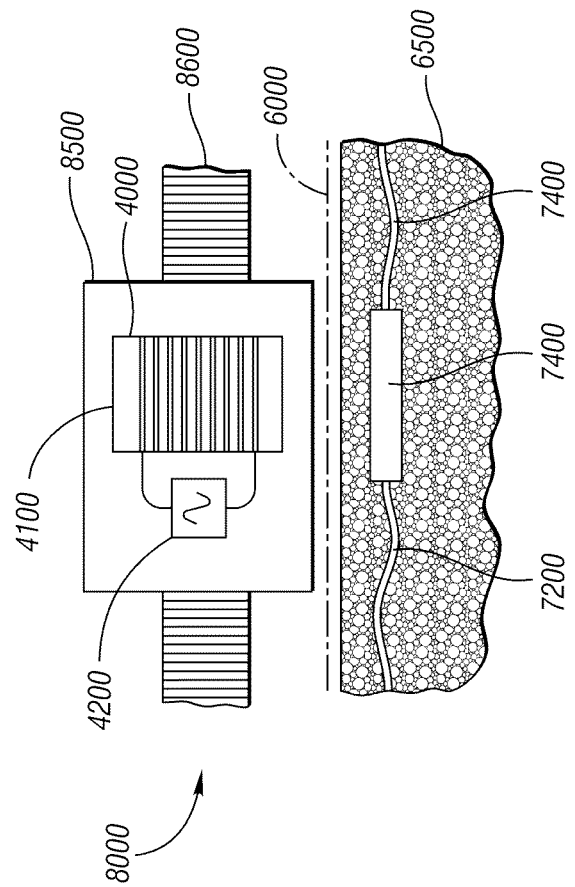
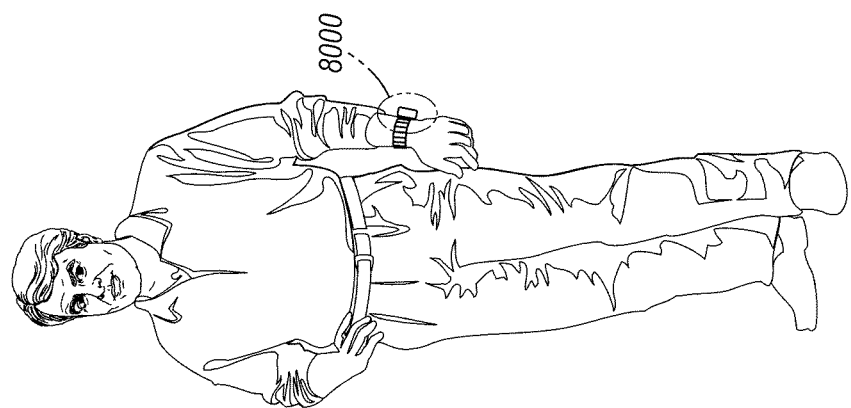
Fig. 9c
Fig. 9b

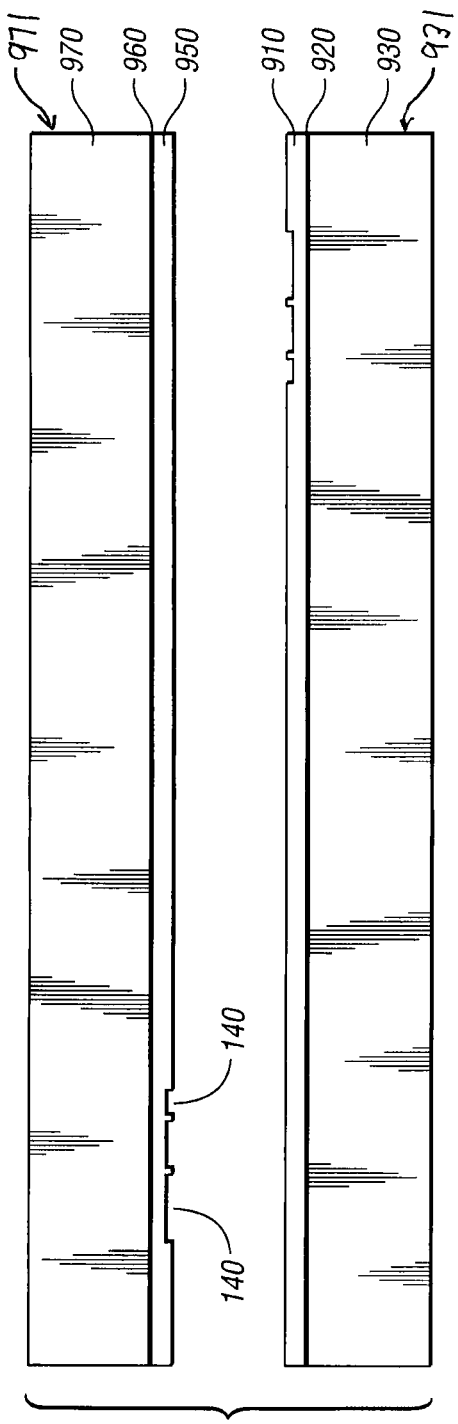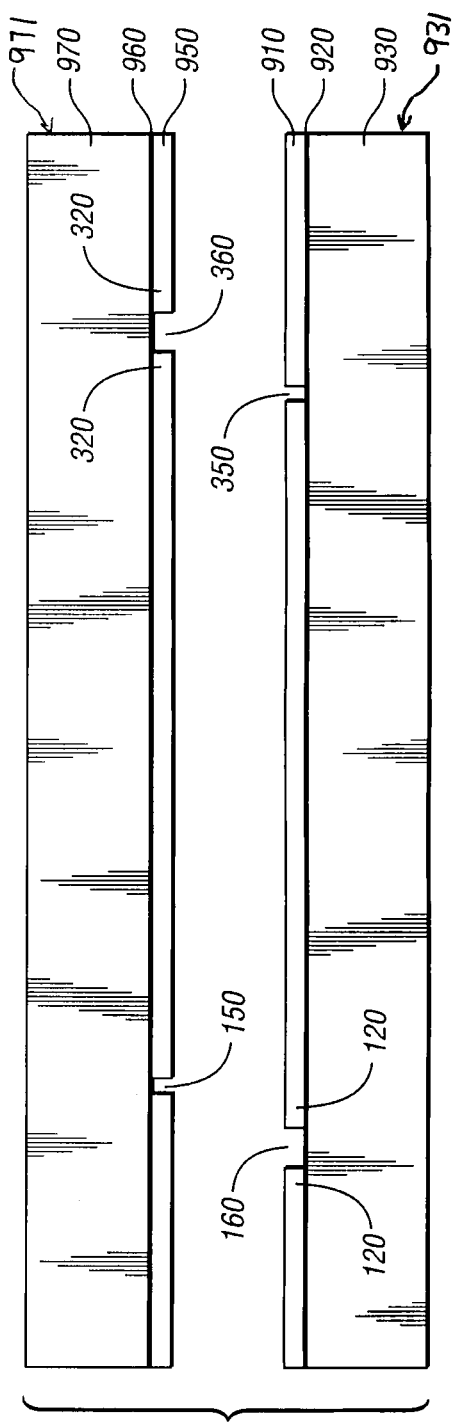

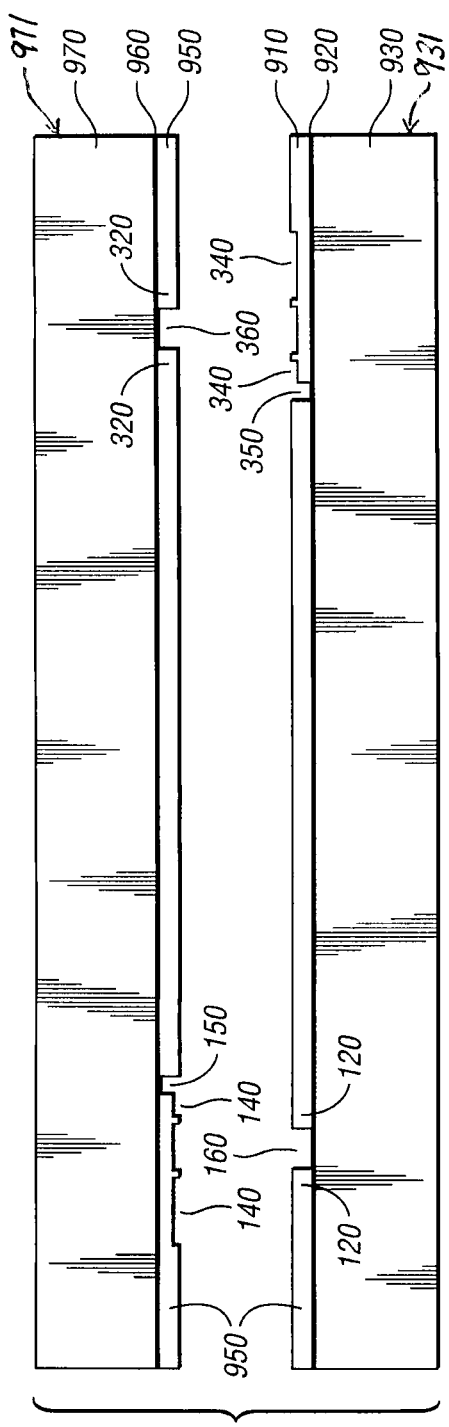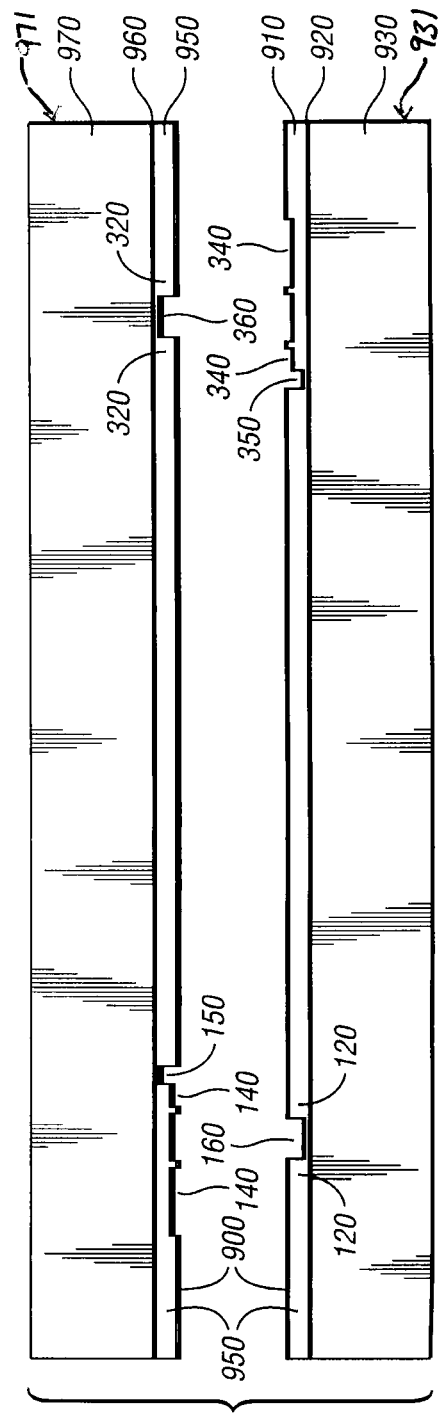

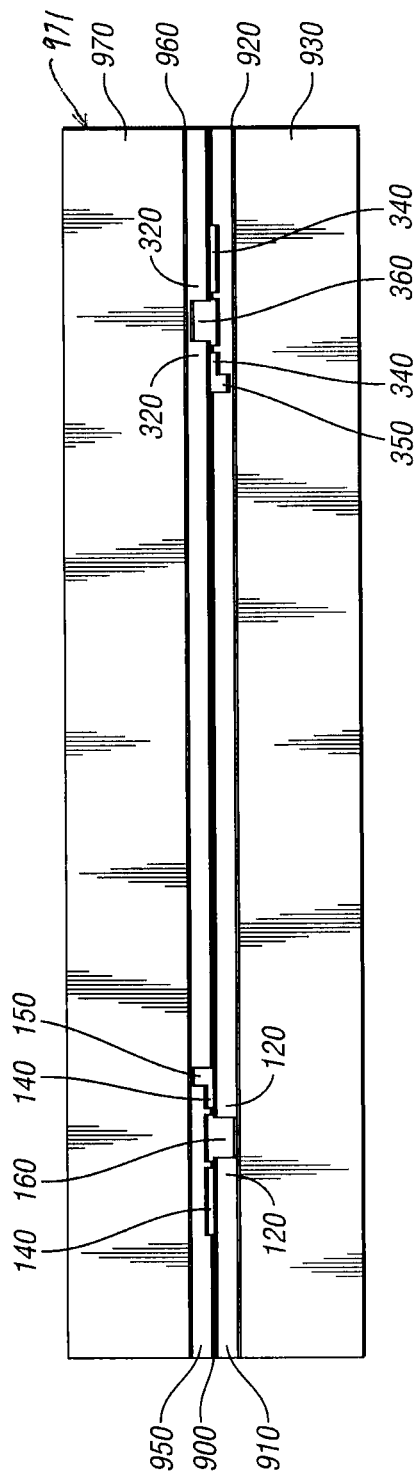
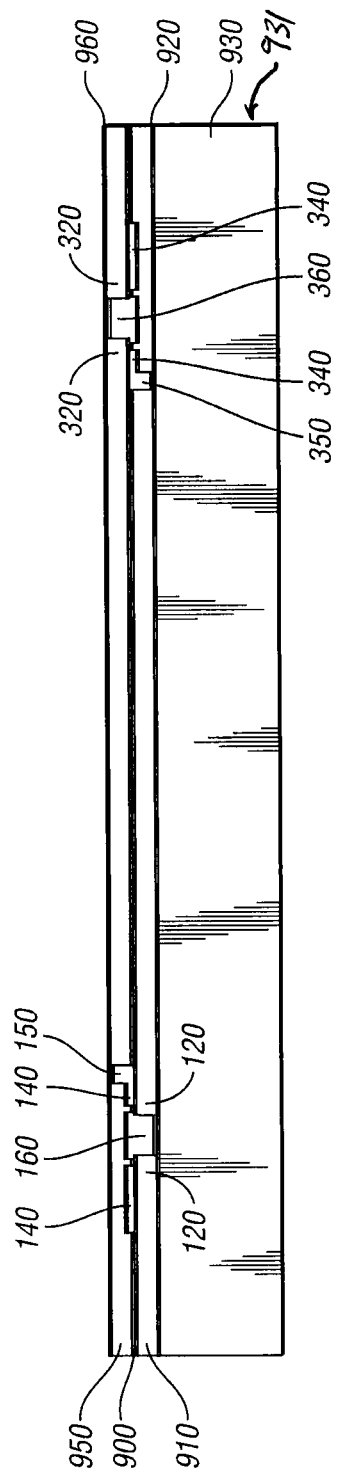

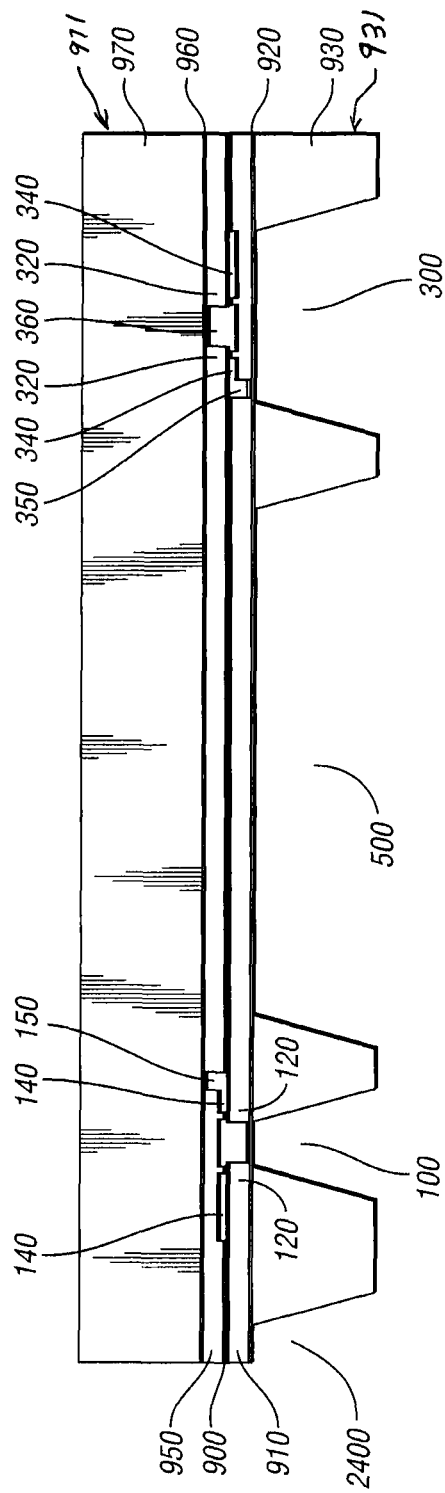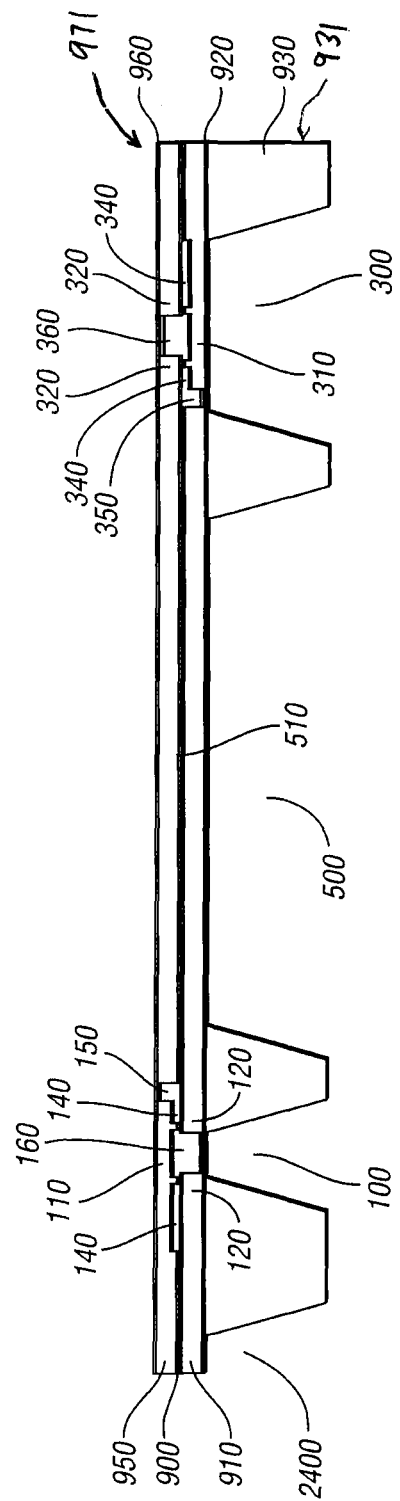

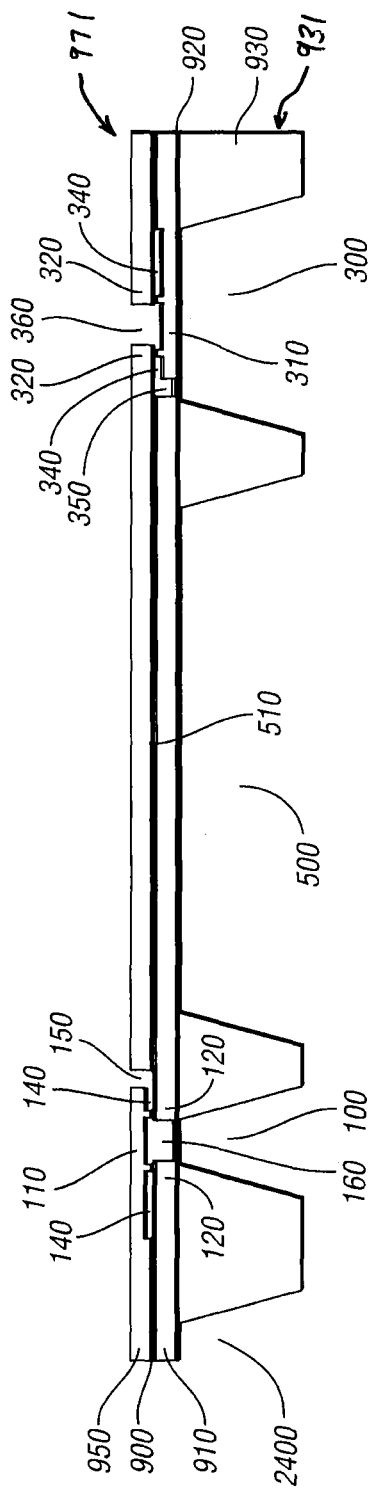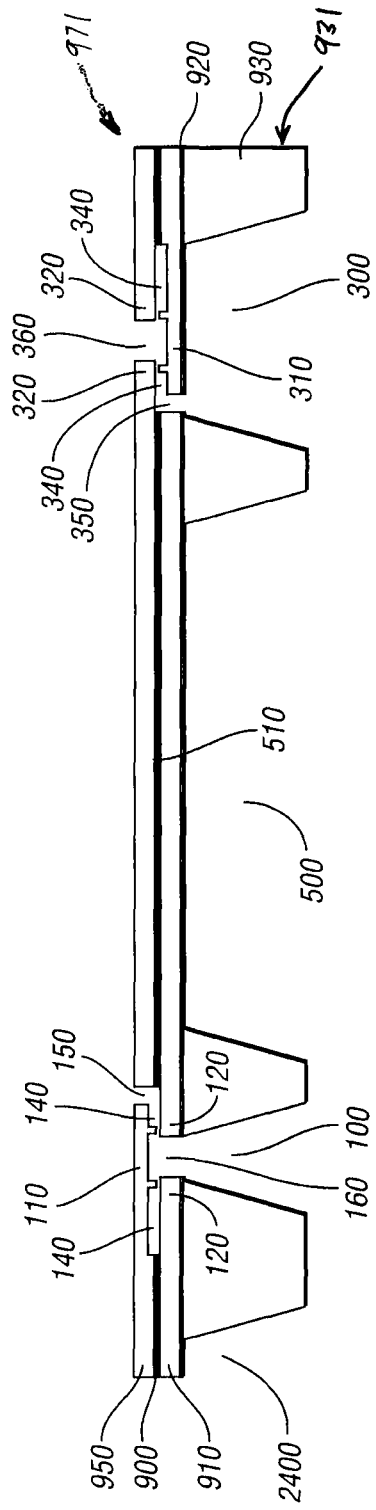

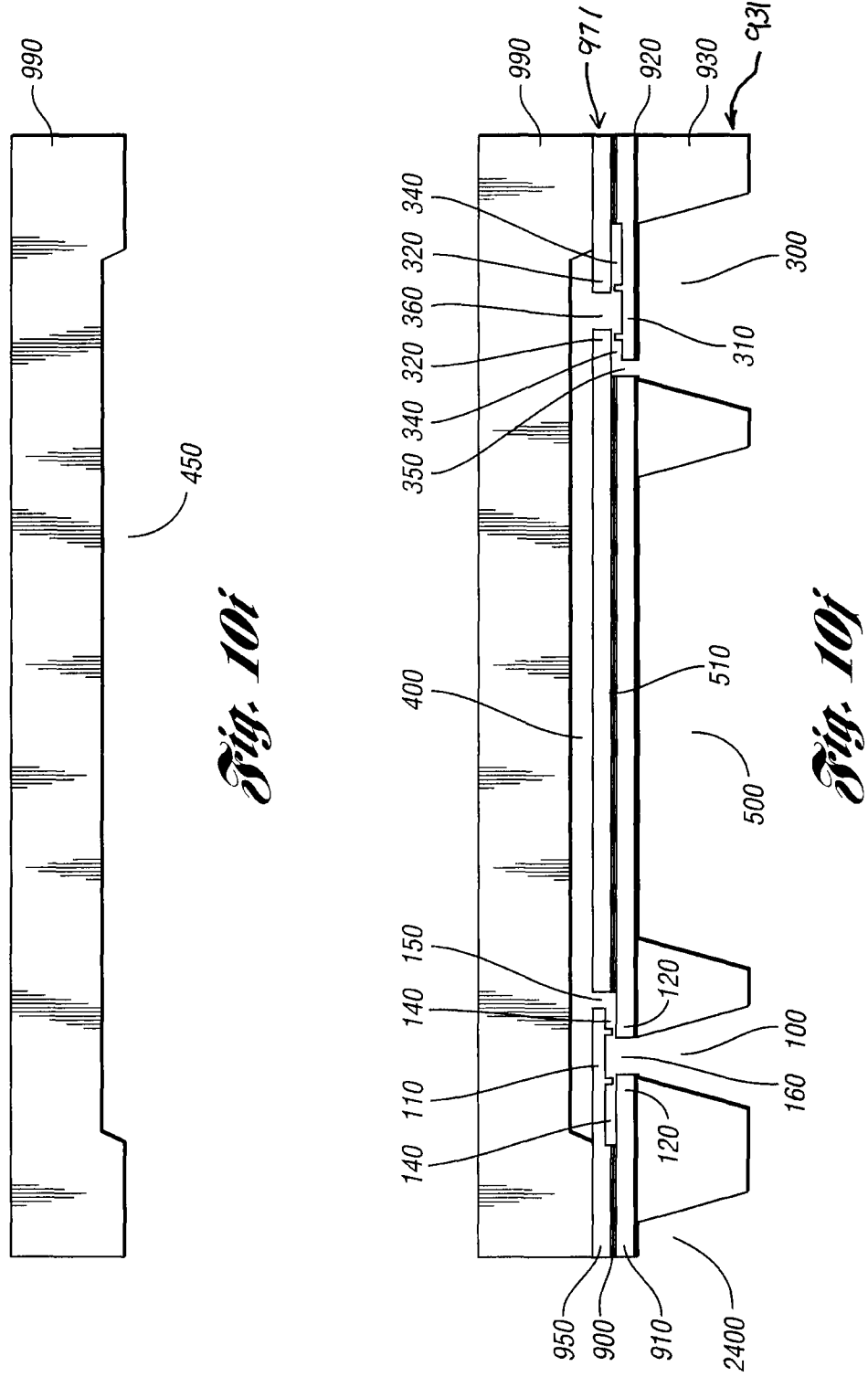

CHECK VALVE DIAPHRAGM MICROPUMP

CROSS REFERENCE TO RELATED APPLICATIONS

This patent application claims the benefit of PCT/US2007/008280, filed Mar. 30, 2007, and U.S. provisional patent application 60/787,332, filed Mar. 30, 2006, entitled "CHECK VALVE DIAPHRAGM MICROPUMP," the entire contents of which are incorporated herein by reference.

FEDERALLY SPONSORED RESEARCH AND DEVELOPMENT

This invention was made with government support under Contract No. ANI-0086020 awarded by the U.S. National Science Foundation. The U.S. government may retain certain rights to the invention.

BACKGROUND OF THE INVENTION

There is relatively high demand for microfluidic systems due to their needed small size, easy portability, and low cost for research, civil, and even some military applications. One core device of a microfluidic system is a micropump. In the past decades, researchers have proposed and developed various micromachining micropump prototypes. Commercially available micropumps made with batch fabrication techniques still under development and may be improved.

One example of a micropump includes a check valve diaphragm micropump. Due to the small stroke of the diaphragm and a comparatively large chamber volume, the diaphragm micropump usually has a relatively small compression ratio (i.e. the ratio of stroke volume to chamber volume). This makes it difficult for such a micropump to deliver gases that have a comparatively high compressibility. It is also difficult to transport liquid that contains air or gases, since the gas pockets accumulate in the chamber and have high compressibility.

For check valve diaphragm micropumps, rigid check valves and diaphragms are unsuitable, since the resistance of the valve is greater than the pressure difference created by the diaphragm actuation mechanism. However, overly flexible check valves and diaphragms are also unsuitable, since leakage would be high and the dynamic response of the micropump would be low, precluding an expected linear working range.

In view of the above, it is apparent that there exists a need for an improved micropump and method of producing micropumps.

BRIEF SUMMARY OF THE INVENTION

In satisfying the above need, as well as overcoming the enumerated drawbacks and other limitations of the related art, the present invention provides a micropump device having a first wafer and a second wafer attached to the first wafer. The first and second wafers define a chamber therebetween having a predetermined volume. A third wafer is attached to the second wafer to define an inlet component and an outlet component in fluid communication with the chamber. At least one of the second and third wafers are formed to define a diaphragm for actuation to change the predetermined volume of the chamber for pumping a fluid.

In some non-limiting examples, the first wafer may be made of one of silicon and glass. In other examples, the second and third wafers may be a silicon device layer with a silicon handle layer attached thereto. A buried layer may be disposed between the silicon device layer and the silicon handle layer. Each of the buried layers may include, for example, one of silicon dioxide and germanium.

The inlet component includes an inlet port and an inlet valve. The inlet valve comprises an inlet valve structure and an inlet valve seat. The inlet valve structure has an edge extending therefrom.

The outlet component comprises an outlet port and an outlet valve. The outlet valve has an outlet valve structure and an outlet valve seat. The outlet valve structure has an edge extending therefrom.

The diaphragm may be configured to be actuated to move away from the chamber during a first predetermined period and to move toward to the chamber during a second predetermined period. The diaphragm may be actuated by one of piezoelectric actuation, electromagnetic actuation, external position-fixed electromagnetic actuation, pneumatic actuation, thermo-pneumatic actuation. A piezoelectric plate may be attached to the diaphragm. The device layer of the third wafer may be configured as a first electrode of piezoelectric actuation and the piezoelectric plate is configured as a second electrode of piezoelectric actuation. For external electromagnetic actuation a coil is disposed about a yoke. The coil may be connected to an AC source, when changing the direction of current periodically, the generated alternating magnetic flux causes the magnetic force of the magnetic material that attached on the diaphragm change, making the diaphragm of the micropump move periodically.

The present invention also includes a method of fabricating a check valve micropump device. The method comprises, for example, forming the inlet valve in the device layers of the third and second wafers and structuring the outlet valve in the device layers of the second and third wafers. Optionally, a diaphragm thinning area may be formed in the device layer of the second wafer, or in the device layer of the third wafer, or in the device layers of the both second and third wafers. A thin film is deposited on the surface of the device layer of either second wafer or third wafer or growing or depositing a thin film on the surface of each device layer of the second and third wafers. The device layers of the third and second wafers are connected. The handle layer of the second wafer is removed. An inlet port, an outlet port, and a diaphragm releasing hole are formed in the handle layer of the third wafer. The exposed buried layers of the second and third wafer are removed. The thin film between the valve structures and valve seats are removed to release the inlet valve structure and the outlet valve structure. A cavity is formed in the first wafer with the size that will cover the diaphragm, the inlet component and outlet component. The method also includes connecting the device layer of the second wafer and the first wafer in such a way that the diaphragm, the inlet valve, and the outlet valve are arranged in a predetermined relationship with the cavity.

In a one example, forming the inlet valve includes providing a gap for the inlet valve structure in the device layer of either second wafer or third wafer, and providing a gap for the outlet valve structure in the device layer of either third wafer or second wafer. In some examples, it also may include forming the diaphragm thinning down structure in the device layer of the second wafer, or in the device layer of the third wafer, or in the device layers of the both second and third wafers.

In a second example, forming the inlet valve includes providing a gap for the inlet valve structure in the device layer of either second wafer or third wafer, and providing a gap for the outlet valve structure in the device layer of either second wafer or third wafer. It also includes forming the inlet valve structure and outlet valve seat in the device layer of the second wafer, and forming the outlet valve structure and inlet valve seat in the device layer of the third wafer.

In a third example, forming the inlet valve includes providing a gap for inlet valve structure in the device layers of both second wafer and third wafer, and providing a gap for outlet valve structure in the device layers of both third wafer and second wafer. It also includes forming the inlet valve structure and outlet valve seat in the device layer of the second wafer, and forming the outlet valve structure and inlet valve seat in the device layer of the third wafer.

In a fourth example, forming the inlet valve includes providing the inlet valve structure and the outlet valve seat in the device layer of the second wafer, and providing the outlet valve structure and the inlet valve seat in the device layer of the third wafer. It also includes forming a gap for the inlet valve structure in the device layer of either second wafer or third wafer, and forming a gap for the outlet valve structure in the device layer of either third wafer or second wafer.

In a fifth example, forming the inlet valve includes providing the inlet valve and the outlet valve seat in the device layer of the second wafer, and providing the outlet valve structure and the inlet valve seat in the device layer of the third wafer. It also includes forming a gap for the inlet valve structure in the device layers of both second wafer and third wafer, and forming a gap for the outlet valve moveable in the device layers of both third wafer and second wafer.

In some examples the thin film may be, but is not limited to, silicon dioxide.

In other examples, connecting the device layers includes attaching the device layers of the third and second wafer in such a way that the respective valve structures are arranged in a predetermined relationship with a respective valve seat. For example attaching the device layers includes connecting by anodic bonding and/or fusion bonding.

In some instances, the diaphragm may be made from the device layers of the second and third wafers.

In other instances, the thickness of the diaphragm is equal or less than that of the remaining device layer.

In still another embodiment the step of forming may include the inlet port and outlet port being aligned to the inlet valve and outlet valve, respectively.

Another example includes the step of forming having the inlet port, outlet port, and the diaphragm releasing hole being aligned to the inlet valve, outlet valve, and the diaphragm thinning area, respectively.

In still other instances, removing the handle layer and the thin film are performed simultaneously.

In another example, forming the cavity includes making the part of the cavity that spans the inlet component deeper than the other part that spans the diaphragm and the outlet section to let the inlet valve structure have more opening space.

In still another example, structuring the cavity includes making the part of the cavity that spans the diaphragm shallower than the other part that spans the inlet and outlet sections to reduce the chamber volume.

In some embodiments connecting the device layer includes connecting by at least one of anodic bonding, fusion bonding, and gluing.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 2 is a side view of one example of three wafers from which the micropump of FIG. 1 may be made;

FIGS. 3A to 3D are cross-sectional views of diaphragm structures of a micropump in accordance with various embodiments of the present invention;

FIGS. 7A and 7B are enlarged views of inlet and outlet component designs;

FIGS. 9B and 9C are schematic diagrams of an electromagnetic micropump used in an implanted application;

FIG. 9D is an exploded concept view of an implanted electromagnetic actuated micropump in accordance with one embodiment of the present invention; and FIGS. 10A to 10J are schematic views of one example of process steps of the fabrication of the micropump shown in FIG. 1.

DETAILED DESCRIPTION OF THE INVENTION

Figure 1:
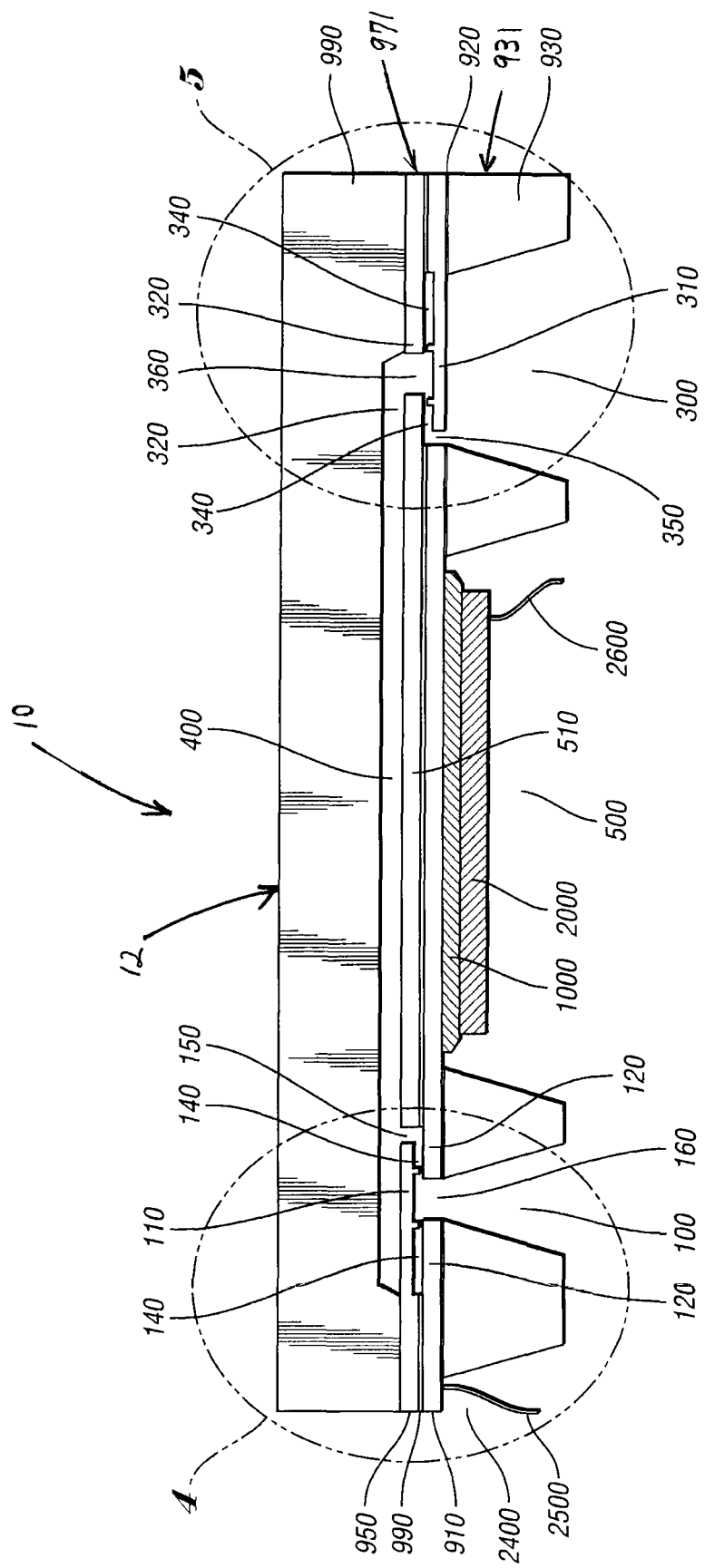
FIG. 1 is the cross-sectional view of a piezoelectric actuated check valve diaphragm micropump in accordance with one embodiment of the present invention.

The performance of a micropump is mainly affected by the material properties, horizontal dimensions, and vertical dimensions. The horizontal dimensions are determined by any appropriate means including, but not limited to, photolithography. The vertical dimensions are controlled within an acceptable error range to make a micropump having a desired performance range.

The present invention takes advantage of advanced microfabrication technologies, such as photolithography, oxidation, deposition, etching, and bonding. Commercially available wafers, Silicon-on-Insulator (SOI) or Epitaxial™ wafers, are used to construct the micropumps. Core components of the micropump, including the diaphragm, the inlet and outlet valves are made within well-defined device layers of the wafers by, for example, a technique called bonding and etching back. These wafers have buried within a layer resistant to etching. Therefore, accurate deep etching may be achieved by automatic etching methods where only the material above the layer is etched while the material underneath the layer is protected.

Typically, the thickness of device layers of two wafers is in the range of 5 to 100 µm, which is one non-limiting example of a desired range for the moveable structures, including check vales and the diaphragm, of a micropump. The cavity that forms the chamber is made in a third glass or silicon wafer. The third layer may be, for example, comparatively thin if a small chamber dead volume is desired Referring now to FIG. 1, a micropump device embodying the principles of the present invention is illustrated therein and designated at 10. As its primary components, the micropump 10 includes a micropump body 12. The micropump body 12 has a chamber 400 with a flexible diaphragm 510, and at least one inlet section 4 and at least one outlet section 5. The inlet section 4 includes an inlet port 100, an inlet valve seat 120, and a moveable inlet valve structure 110. The outlet section 5 includes an inlet port 300, a moveable outlet valve structure 310, and an outlet valve seat 320. The inlet section 4 is designed in such a way that it only allows flow in one direction to pass through that correspond to a related pressure difference and prevents opposite direction flow to pass through. The outlet section is similarly designed. The chamber 400 spans the inlet section 4, the diaphragm 510, and the outlet section 5.

The diaphragm 510 may, for example, be driven by a periodic actuation method including, but not limited to, piezoelectric actuation, electromagnetic actuation, pneumatic actuation, and thermo-pneumatic actuation, which directly or indirectly transfers electrical energy into mechanical movements. Piezoelectric actuation, as shown in FIG. 1, includes attaching a piezoelectric plate 2000 onto the diaphragm 510 with, for example, conductive glue 1000. The wire 2500 for actuating the piezoelectric plate 2000 is connected through an electrode opening hole 2400. The other wire 2600 is directly connected to the piezoelectric plate 2000.

During a first half period of the piezoelectric actuation on the diaphragm 510, the diaphragm 510 is driven away from the chamber 400, reducing a chamber 400 pressure, which moves the inlet valve structure 110 away from the inlet valve seat 120 while allowing the outlet valve structure 310 to remain in contact with the outlet valve seat 320. This results in the pumping medium being drawn into the chamber 400 from the inlet port 100 and through the opened gap between the inlet valve structure 110 and the inlet valve seat 120. During a second half periods of the periodic actuation method applied to the diaphragm 510, the diaphragm 510 is driven towards to the chamber 400, increasing chamber 400 pressure. This makes the inlet valve structure 110 move back into contact with the inlet valve seat 120 to close the inlet section 4 while moving the outlet valve structure 310 away from the outlet valve seat 320, resulting in the pumping medium being driven out of the chamber 400 through the outlet port 300 via a gap between the outlet valve seat 320 and the outlet valve structure 310.

The micropump body shown in FIG. 1 is made from three wafers as best shown in FIG. 2. In this embodiment, a top wafer 990 could be either a glass or a silicon wafer. A middle wafer 971 has a buried layer 960 sandwiched by a device layer 950 and a handle layer 970. A bottom wafer 931 has a buried layer 920 sandwiched by a device layer 910 and a handle layer 930. The middle and bottom wafers 971 and 931 can be, for example, commercially available Silicon-on-Insulator wafers or epitaxial wafers. The major parts of the micropump include the inlet valve, the outlet valve, and the diaphragm. For example, the diaphragm 510 shown as in FIG. 1 is made from the device layers 950 and 910 of the middle and bottom wafers.

While the piezoelectric actuated micropump shown in FIG. 1 is one non-limiting example of a device that can be made from the three wafers in FIG. 2, other possible devices having, for example, different diaphragm, different inlet and outlet valves, a different thin film, different chamber, different actuation methods, and different materials are possible.

The present invention also includes a method of making a micropump. As shown in the example of FIG. 1, the method includes providing a thin layer 900 to connect the device layers of 950 and 910 of middle and bottom wafers 971 and 931 according to a pre-aligned relationship. Etching to remove a handle layer 970 (now shown) and forming a diaphragm releasing hole 500 in a handle layer 930 of the bottom wafer 931. Any exposed buried layers 920 and 960 are removed from the middle and bottom wafers 971 and 931.

Since etching of the handle layers automatically stops when chemicals or plasma meets the buried layers 920 and 960, the thickness of the diaphragm is the sum of the thickness of the device layers 950 and 910 of the middle wafer and bottom wafer 971 and 931. The horizontal dimensions of the diaphragm 510 are determined by any appropriate photolithography technology as noted above. To optimize micropump performance for the different actuation mechanisms used in various applications, it may be desirable for the micropump to have a thinner diaphragm.

Figure 3C:
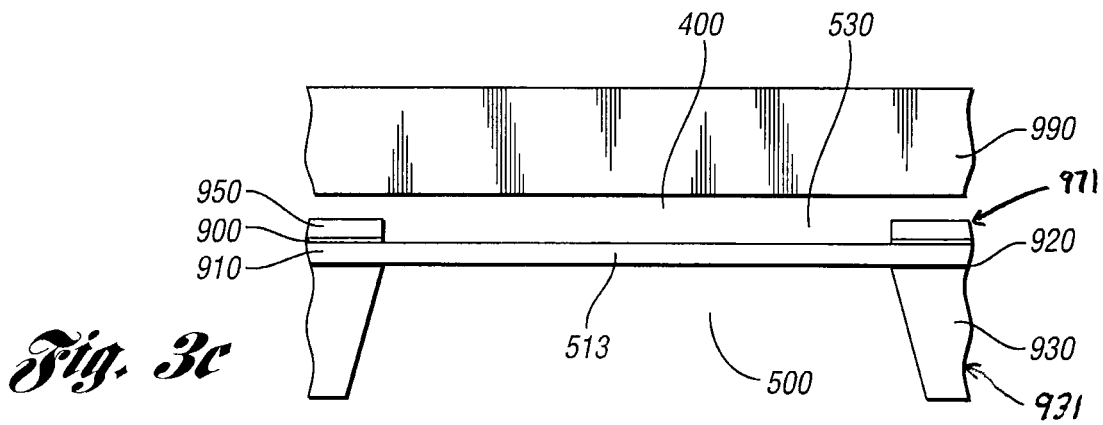

The diaphragm can be made thinner as illustrated in FIGS. 3A to 3D. Turning to FIG. 3A, the diaphragm 511 is comprised only of the device layer 950 of the middle wafer 971. Compared to the micropump body in FIG. 1, this example removes a diaphragm thinning area 520 (i.e., removing the related device layer 910 of bottom wafer corresponding to the size of the diaphragm) before connecting the middle and bottom wafers 971 and 931. For an even thinner diaphragm, best shown in FIG. 3B, a diaphragm 512 may be composed of a partial thickness of the device layer 950 of the middle wafer 971, which is achieved by applying an additional thinning down process in a diaphragm thinning area 525 of the device layer 950. For Example, a time control method may be used before connecting the middle and bottom wafers. The additional thinning down process of the device layer 950 is always shallow such that a time control etching method is in an acceptable accurate range.

Figure 3B:
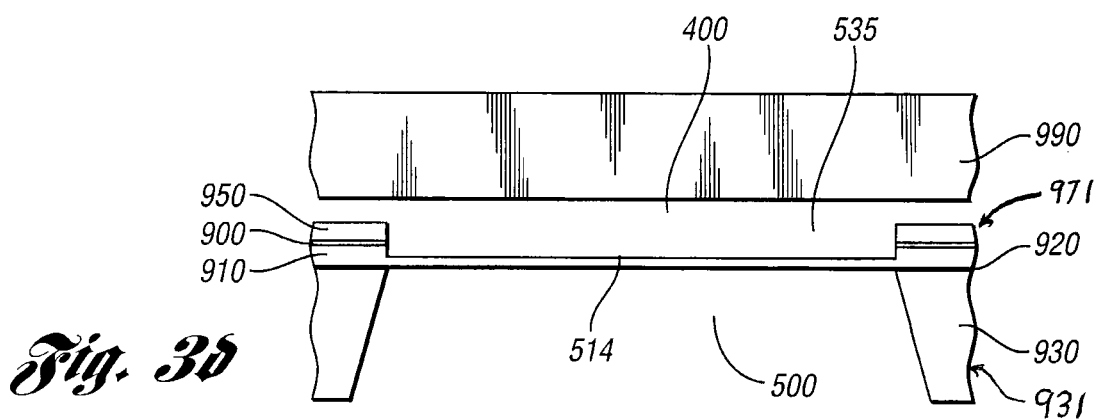

Similarly, instead of adopting the device layer 950 of the middle wafer shown in FIGS. 3A and 3B as the diaphragm, the diaphragm 513 and 514 shown in FIGS. 3C and 3D, respectively, can include only the device layer 910 of the bottom wafer 931 or even a partial thickness of it as well. These new two cases, have a bigger chamber due to the volume of the thinning areas 530 and 535 than the previous three cases shown in FIGS. 1, 3A, and 3B. In order to reduce the chamber volume as discussed, the geometry of chamber 400 should be coordinately optimized, which will be discussed later.

Turning now to the inlet and outlet sections 4 and 5. As shown in FIG. 1. The inlet section 4 includes an inlet port 100 aligned with an inlet valve. The inlet valve includes the moveable inlet valve structure 110, the inlet valve seat 120, and an inlet valve hole 160. The inlet port 100, inlet valve hole 160, the inlet valve seat 120, and the inlet valve structure 110 are aligned in sequence. An inlet valve gap 140 is provided to avoid the moveable inlet valve structure 110 sticking to the valve seat 120 when connecting the middle and bottom wafers in fabrication.

Figure 4A:
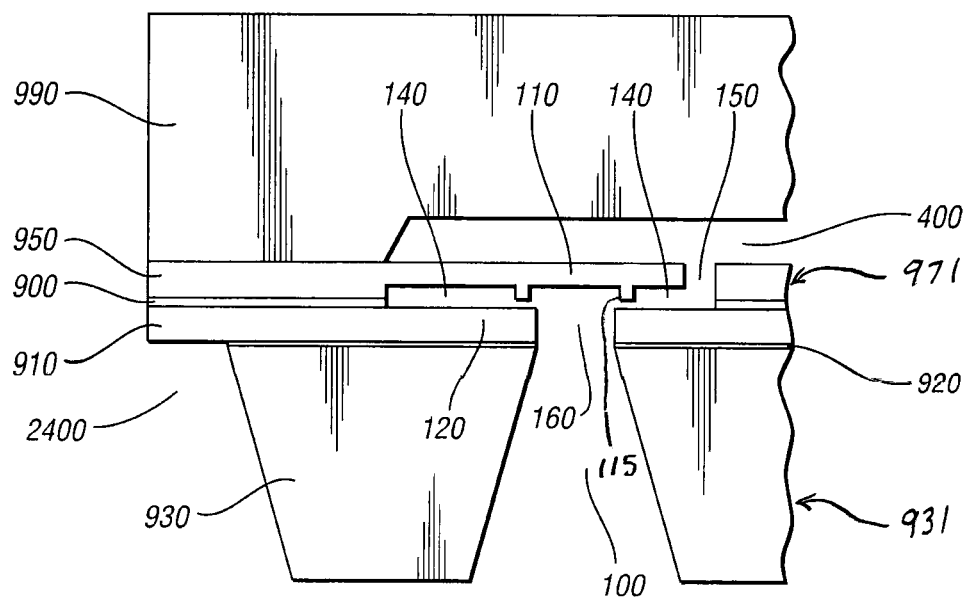
FIG. 4A is an enlarged view of an inlet component of FIG. 1.

Optionally, an inlet valve edge 115 extends from the inlet valve structure 110 toward the inlet valve seat 120. In one instance, a height of the inlet valve edge 115 is less than the inlet valve gap 140. The inlet section 4 is designed in such a way that it only allows the flow from the inlet port 100 to the chamber only when the pressure of the chamber 400 is lower than that of the inlet port 100 and prevents inverse flow to pass through when an opposite pressure difference exists. The inlet valve gap 140 (without any pressure difference) between the inlet valve structure 110 and inlet valve seat 120 is the thickness of the thin film 900, which is so small that any leakage will be minimal. Detail information about the inlet section 4 is shown in FIGS. 4A and 4B.

Figure 5A:
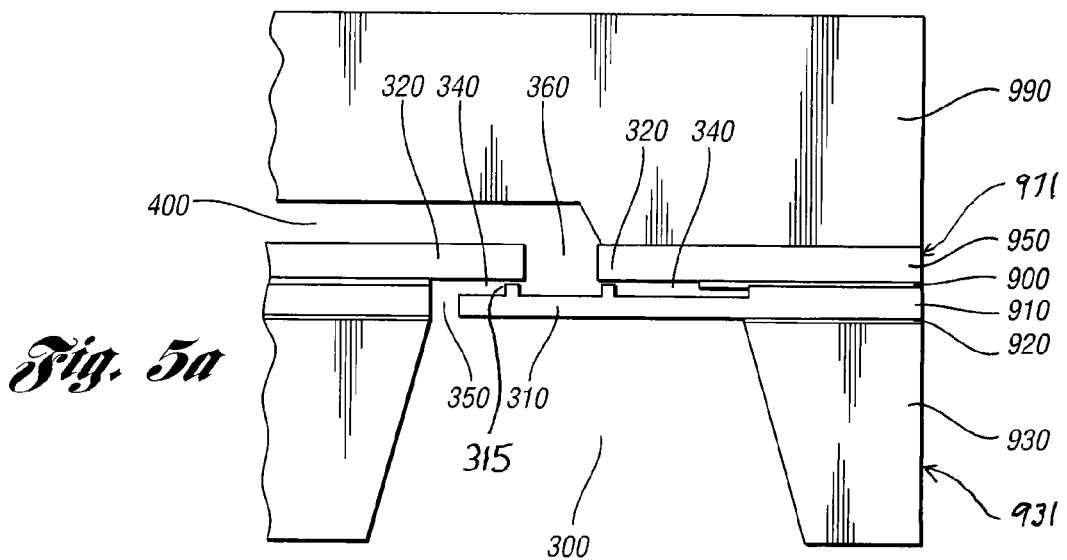
FIG. 5A is an enlarged view of an outlet component of FIG. 1.

Returning to FIG. 1, the outlet section 5 includes an outlet port 300 and an outlet valve. The outlet valve is includes the moveable outlet valve structure 310, the outlet valve seat 320, and the outlet valve hole 360. The outlet port 300, outlet valve hole 360, the outlet valve seat 320, and the outlet valve moveable structure 310 are aligned in sequence. An outlet valve gap 340 is provided to avoid the moveable outlet valve structure 310 from sticking to the outlet valve seat 320 when connecting the middle and bottom wafers in fabrication. Optionally, an outlet valve edge 315 extends from the outlet valve structure 310 toward the outlet valve seat 320. In one instance, a height of the outlet valve edge 135 is less than the outlet valve gap 340. The outlet section 4 is designed in such a way that it only allows the flow from the chamber 400 to the outlet port 300 only when the pressure of the chamber 400 is higher than that of the outlet port 300, and prevents reverse direction flow. The initial outlet valve gap 340 between the outlet valve moveable structure 310 and outlet valve seat 320 is the thickness of the thin film 900, which is so small that any leakage of the valve is minimized. The outlet valve seat 320 is made, for example, from the device layer 950 of the middle wafer, which may be flexible to some degree. To make it as stiff as possible to improve the outlet valve performance, three edges of the valve seat 320 are designed to be connected to the top wafer 990, only leaving the fourth edge, above which is part of the chamber 400, disconnected. The outlet section 5 is shown in detail in FIGS. 5A and 5B.

Figure 4B:
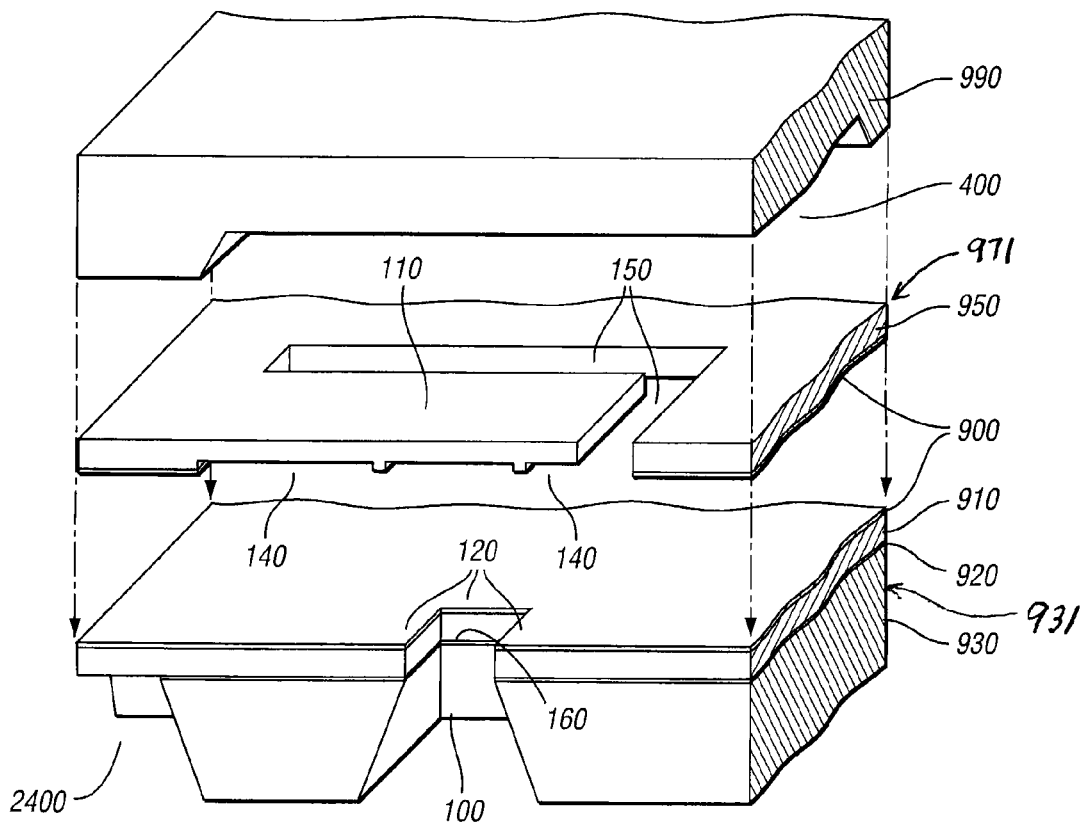
FIG. 4B is an exploded view of the inlet component of FIG. 4A.
Figure 5B:
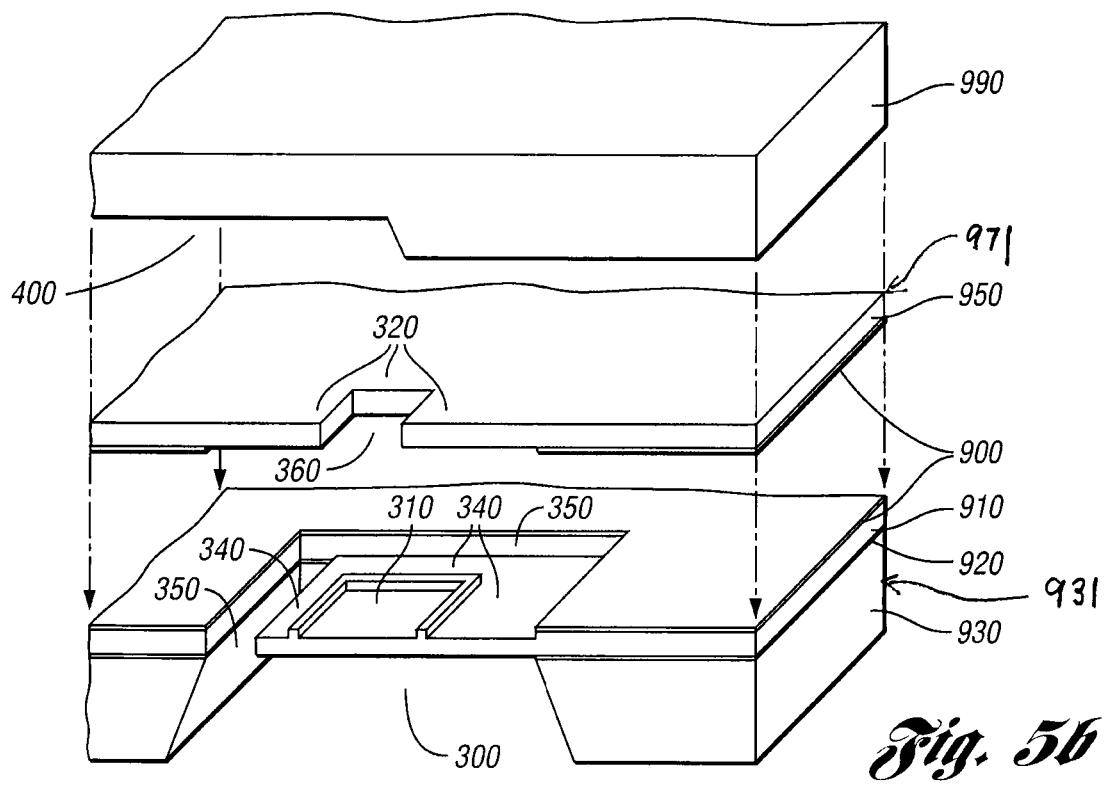
FIG. 5B is an exploded view of the outlet component of FIG. 5A.
Figure 6A:
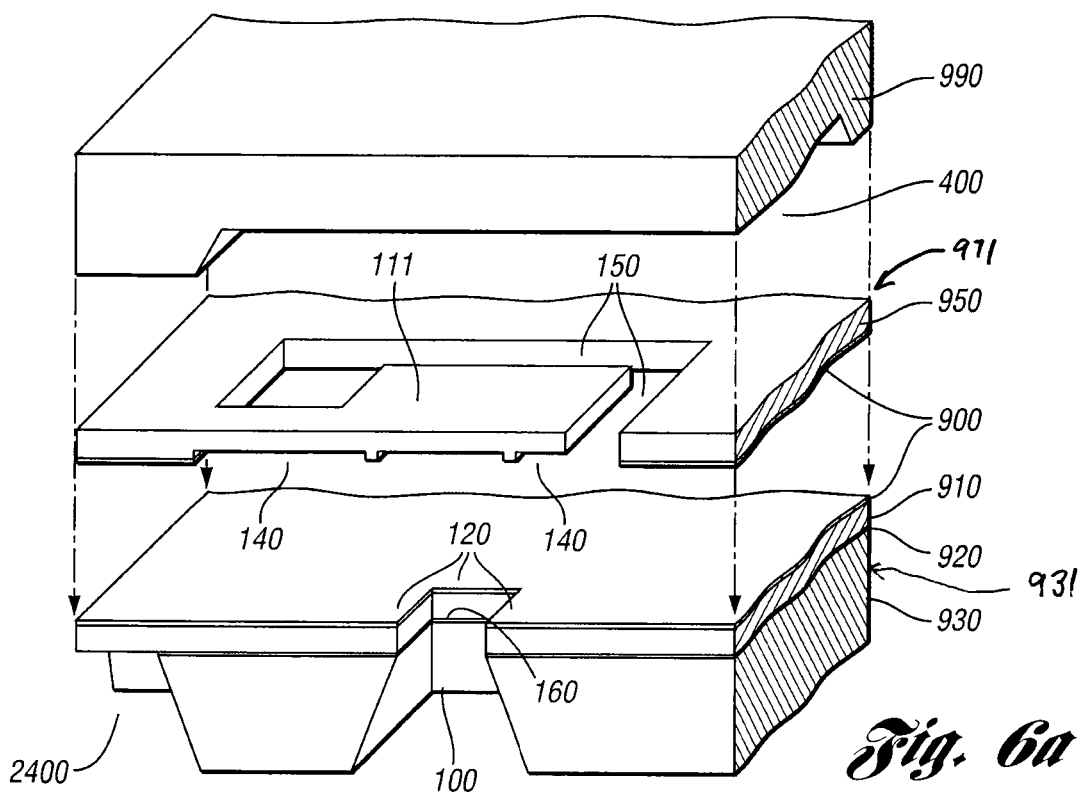
FIGS. 6A and 6B are exploded views of inlet and outlet valves in accordance with another embodiment of the present invention.
Figure 6B:
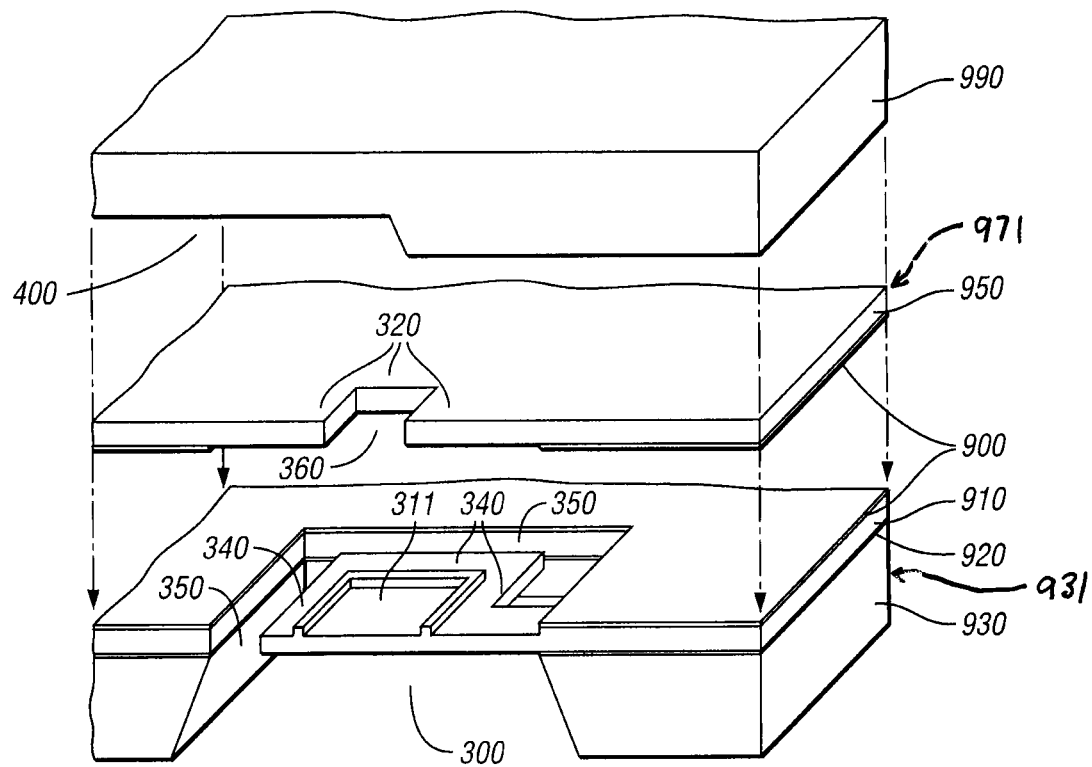

The inlet and outlet valve structures 110 and 310 shown in FIGS. 4B and 5B are rectangular cantilevers. Other examples include valve structures 111 and 311, having smaller necks, shown in FIGS. 6A and 6B.

Figure 7B:
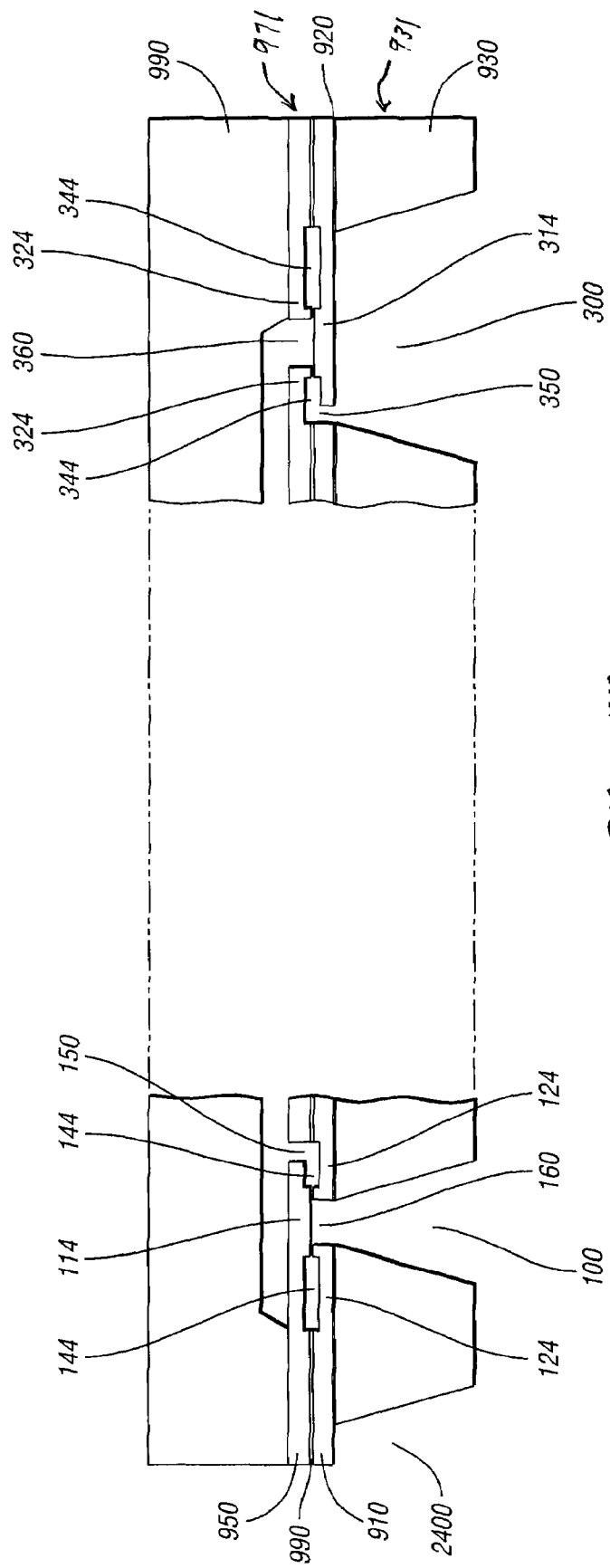

Returning to FIG. 1, the inlet valve gap 140 is shown in the device layer 950 of the middle wafer 971 while the outlet valve gap 340 is shown in the device layer 910 of the bottom wafer 931 before connecting the middle and bottom wafers. The valve gaps may be in any other layers as well. As best shown in FIG. 7A, an inlet valve gap 142 has been made in the device layer 910 of the bottom wafer 931 while an outlet valve gap 342 has been made in the device layer 950 of the middle wafer 971 before connecting the middle and bottom wafers. Another example is shown in FIG. 7B, in which valve gaps 144 and 344 have been made in both device layers 950 and 910 before connecting the middle and bottom wafers 971 and 931. Various combinations of above examples are also possible.

Turning now to the thin film 900, this layer may be a sacrificial material that can be dissolved by etching or other mechanisms without affecting any other structures. The thickness of the thin film 900 is, for example, in the range of sub microns to several microns. This allows chemical or plasma etching. After the thin film is grown or deposited on the surface of either device layer 950 or 910 of the middle and bottom wafers or on both surface of the device layer 950 and 910, the middle and bottom wafers 971 and 931 are connected in a predetermined alignment. The valve structures are connected with the related valve seats by bonding. The thin film 900 between the inlet valve structure 110 and inlet valve seat 120 and between outlet valve structure 310 and outlet valve seat 320 is then dissolved or otherwise removed. The etching rate is usually so slow that its effects on other structures can be neglected. One non-limiting example of an appropriate material for the thin film 900 is thermal silicon dioxide.

In FIG. 1, the chamber 400 is formed by connecting the top wafer 990, having a cavity 450, onto the exposed device layer 950 of the middle wafer 971 after the handle layer 970 and buried layer 960 are removed. The depth of the cavity 450, for example from 5 microns to 100 microns, is one dimension defining the chamber volume. If the volume of the chamber 400 is too large, the compression ratio of the micropump may be too small to satisfy, for example, self-priming. Another factor considered in the chamber design is that the inlet valve structure 110 needs enough space to freely move, which means a larger chamber improves inlet valve performance, especially when the delivered medium contains particles. However, this reduces the large compression ratio. Therefore, a number of other cavities, which will later form the chamber 400, are proposed to satisfy both above requirements. In one embodiment, the compression ratio is defined as $DV/V_0$. DV is the volume change and $V_0$ is the initial volume or the dead volume. A compression ratio for the micropump is at least about 0.1 and preferably about 5% for self-priming. A compression ratio range may be between about 0.1% and about 200%.

Figure 8A:
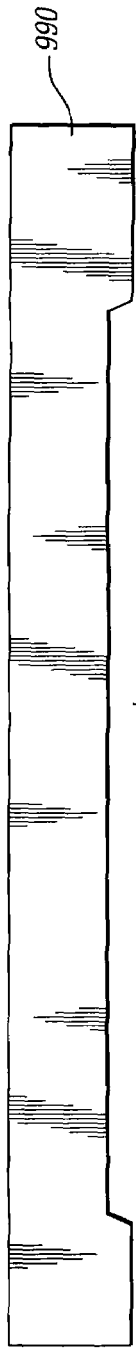
FIGS. 8A to 8D are side views of cavities formed for the chambers of the micropump in accordance with various embodiments of the present invention.
Figure 8B:
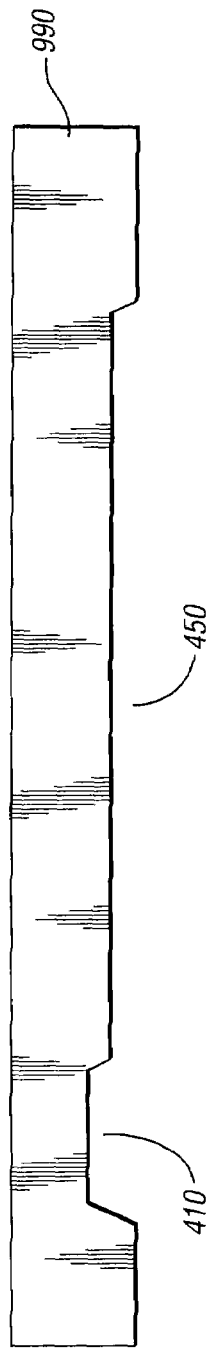
Figure 8C:
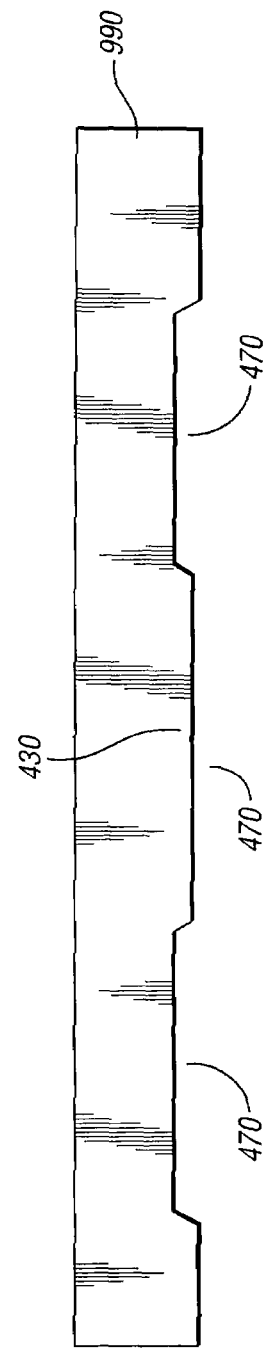
Figure 8D:
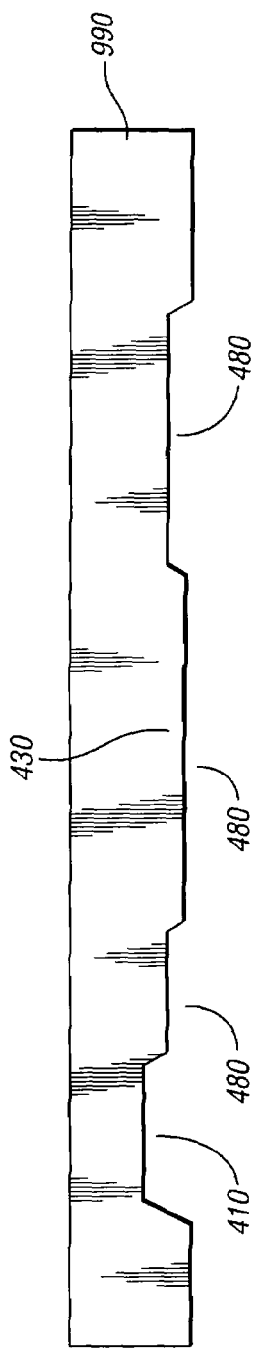

The cavity 450 in FIG. 8A has similar shape to that of the micropump 10 in FIG. 1. In order to have more space for the movement of the inlet valve structure 110, instead of deepening the entire cavity 460, it is possible to locally remove part of the cavity 410 adjacent the inlet valve structure 110 a shown in FIG. 8B. In order to have a small chamber volume, one example is shown in FIG. 8C optimized to leave a block 430 in the cavity 470. A combination of the examples of FIGS. 8B and 8C are also possible as shown in FIG. 8D.

As noted above, the micropump 10 shown in FIG. 1 may be actuated by piezoelectric methods, by mounting a piezoelectric plate or disc 2000 onto the diaphragm 510 with, for example, conductive glue 1000. An electrode opening hole 2400 serves one electrode pad and the unglued piezoelectric material surface serves as the other electrode pad. A wire 2500 and wire 2600 connect the pad, respectively to an AC electric source. Piezoelectric actuated micropumps can be used to drug delivery systems, micro reactor systems, micro analysis systems, and medicine development. Other methods, such as pneumatic, thermo-pneumatic, and electromagnetic actuation are also preferred actuation methods.

Figure 9A:
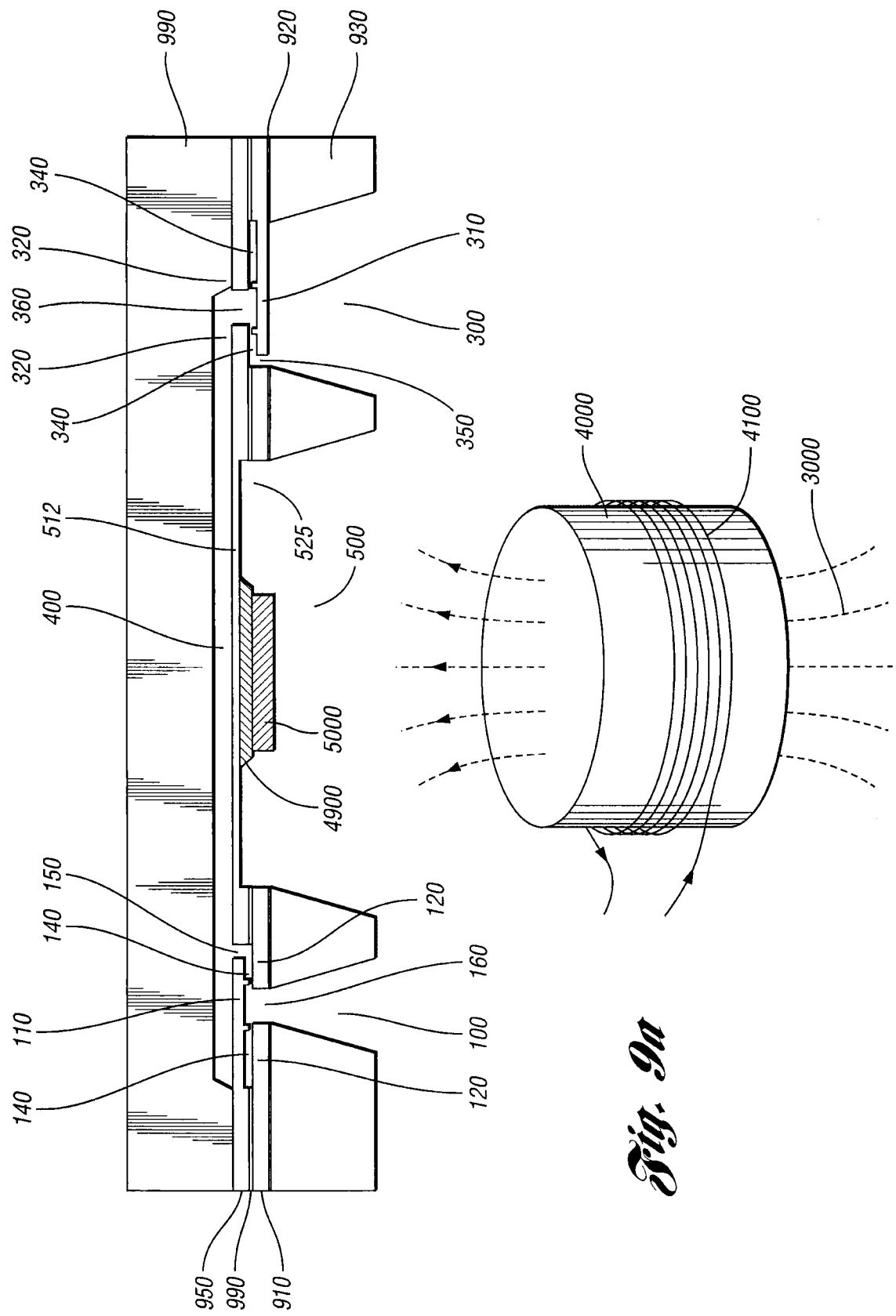
FIG. 9A is the cross-sectional view of an electromagnetic actuated check valve diaphragm micropump in accordance with one embodiment of the present invention.
Figure 9B:
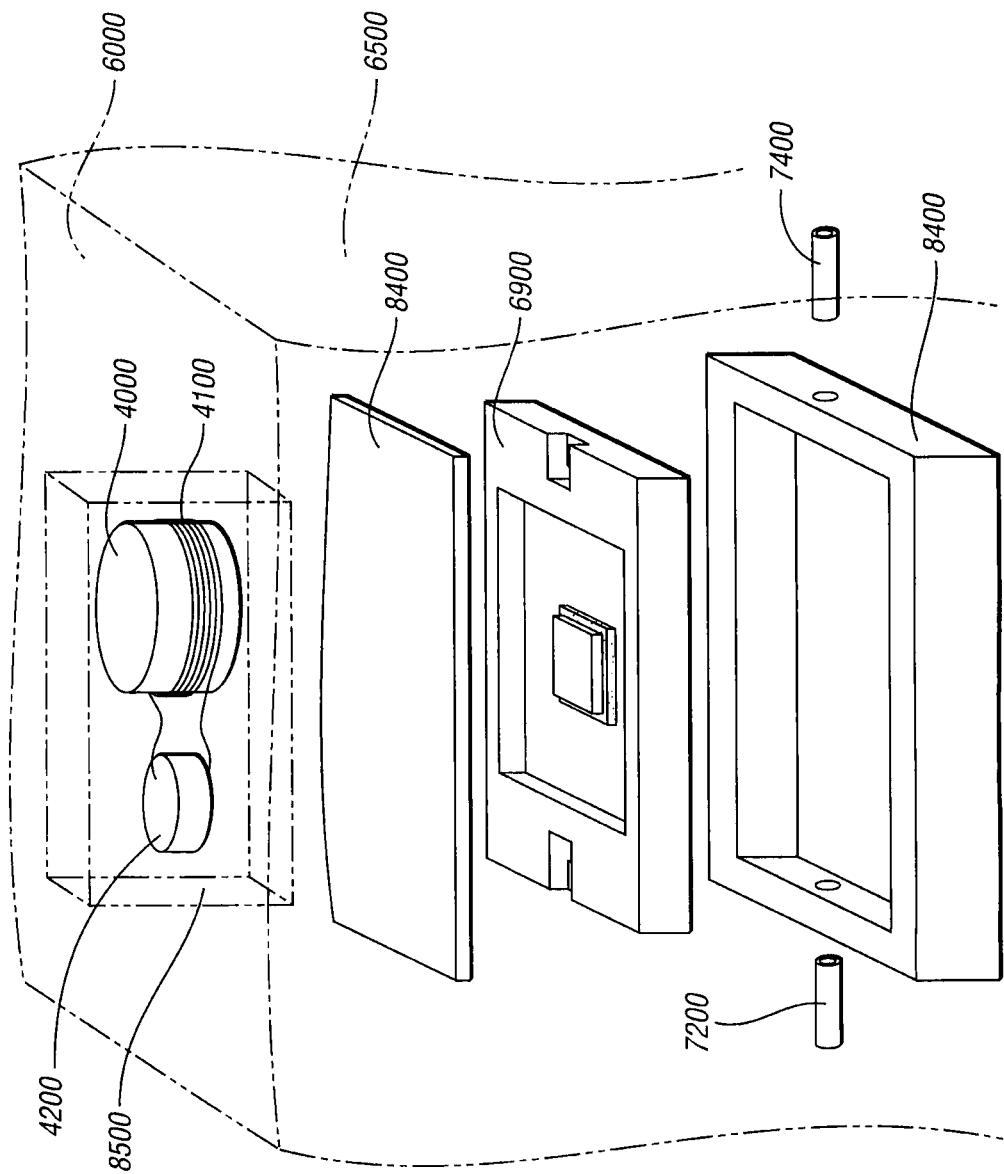

As shown from FIG. 9A to 9C, a micropump actuated by an electromagnetic mechanism is applied to implanted applications. Like a piezoelectric actuated micropump attached a piezoelectric material on its diaphragm, an electromagnetic actuated micropump has magnetic material 5000 attached to the diaphragm as shown in FIG. 9A. Moreover, a position fixed extra device that provides an alternating magnetic flux is necessary to complement electromagnetic actuation. The extra device can be a yoke 4000 surrounded by a coil 4100. When a current is applied on the coil 4100, generating magnetic flux 3000 in up direction, the attractive or repulsive magnetic force between the fixed device and the magnetic material 5000 attached on the diaphragm 511, causes the diaphragm 512 to move towards to or away from the chamber 400. When a current with opposite direction is applied on the coil 4100, generating magnetic flux 3000 in down direction, an opposite magnetic force is generated between the fixed device and the magnetic material 5000, resulting the diaphragm 510 moving away from or towards to the chamber 400.

One example of an application for such a micropump is for implanted drug delivery. FIGS. 9B-9D give an example of implanted drug delivery application. In FIG. 9B, like wearing a watch, a patient carries an external device in his wrist through a band, under which is the implanted micropump chip. Details are shown in FIG. 9C. The yoke 4000 with coil 4100 and the power supply 4200 including battery and driven circuits are packaged in a container 8500, which is fixed on the wrist by the band 8600. Under the skin 6000 is the patient body tissues 6500, in which the packaged electromagnetic micropump 7000 is implanted. The inlet catheter 7200 conducts the reservoir of the drug and the packaged micropump 7000, and the outlet catheter 7400 goes the place where the drug should be sent to. FIG. 9D shows an exploded view of an implanted electromagnetic actuated diaphragm micropump.

Since the power is transmitted through magnetic field, no direct power supply together with the micropump chip is required. The advantages of electromagnetic actuated micropump include: it doesn't require the micropump to carry batteries, no surgery required to change any battery, delivery time and quantity are remotely controlled through off-body components, and it is more convenient for a doctor and even a patient to administer and monitor daily therapy.

On embodiment of a method for making the micropump begins with three commercially available wafers, the top wafer 990, either glass or silicon wafer, the middle Silicon-on-Insulator (SOI) wafer 971 with a buried silicon oxide layer 960 sandwiched by a silicon device layer 950 and a silicon handle layer 970, and the bottom SOI wafer 931 with a buried silicon oxide layer 920 sandwiched by a silicon device layer 910 and a silicon handle layer 930. The thickness of the device 950 and 910 typically are, for example, from 5 to 100 microns. It should be noted that other materials than silicon oxide may be used including, but not limited to germanium.

Form structures in the device layers 950 and 910 of the two SOI wafers 971 and 931, which will later form the inlet valve and outlet valve. Provide the inlet gap 140 in the device layer 950 of the middle wafer 931 and form the outlet gap 340 in the device layer 910 of the bottom wafer 931 as shown in FIG. 10A-1. The gaps 140 and 340 will avoid the constructed area connecting when the device layers 910 and 950 are connected with each other in later procedures, which is necessary to allow movement of the valve structures 110 and 310. Turning to FIG. 10A-2, make a structure 150 that defines the inlet valve structure 110 and an outlet valve hole 360 that defines the outlet valve seat 320 in the device layer 950 of the middle wafer 971. Make a structure 350 that defines the outlet structure 310 and an inlet valve hole 160 that defines the inlet valve seat 120 in the device layer 910 of the bottom wafer 931. Form an inlet gap 140 in the device layer 950 of the middle wafer 971 and an outlet gap 340 in the device layer 910 of the bottom wafer 931 as in FIG. 10B.

After structuring the valve hole 160 and 360, the valve seat 120 and 320 are formed. Wet chemical etching and plasma etching are two possible, but non-limiting etching methods. The maximum etching depth is the same as the device layer 910 or 950 when making the valve hole 160 and 360 and the structure 150 and 350. The depth of the gaps 140 and 340 are usually less than the thickness of the device layer.

After making the structures for the inlet and outlet valves in the device layers 950 and 910 of the middle and bottom SOI wafers, deposit or grow a thin film 900 on each of the device layer 950 of the middle and the device layer 910 of the bottom wafer as shown in FIG. 10C. The thin film 900, such as silicon dioxide, should have the similar property as the buried layer 920 or 950. After the thin film 900 is deposited or grown, connect the device layers 950 and 910 of the middle and bottom wafer in such a way that the inlet valve moveable 110 and the inlet valve hole 160, and the outlet valve structure 310 and outlet valve hole 360 are aligned, as shown in FIG. 10D. Silicon fusion bonding and anodic bonding are two possible but non-limiting connection methods.

The next fabrication process is to remove whole handle layer 970 of the middle wafer 971 and to form the inlet port 100, outlet port 300, diaphragm releasing hole 510, and electrode opening hole 2400. For example, a plasma etching method may be used to remove the handle layer 970 of the middle wafer. Since the buried layer 960 and the thin film layer 900 are almost immune to the plasma that fast etches silicon, the plasma etching stops when it meets the buried layer 960 and 900. Thus the pattern made in the device layer 950 and 910 in previous steps is not etched. Before plasma etching, a chemical mechanical grinding method may optionally be used to thin down the handle layer 970 and remove most of the handle layer 970. The chemical grinding should be stopped before reaching the buried layer 960 of the middle wafer 971. FIG. 10E-1 shows the cross-section view of the structure after the whole handle layer 970 of the middle wafer is removed. Instead of using plasma etching, chemical etching is an alternative method. Like plasma etching, chemical etching stops when the chemical solution meets the buried layer 960 and the thin film 900. Now form the inlet port 100, the outlet port 300, the diaphragm releasing hole 510, and the electrode opening hole 2400 by plasma or wet chemical anisotropic etching. All of these should be respectively aligned to the inlet valve hole 160, outlet valve hole 360, and the preferred diaphragm position, as best shown in FIG. 10F.

The above procedures working with the handle layers of the middle and bottom wafers 971 and 931 may be executed in different sequences as appropriate. FIG. 10E-2 shows one example where the inlet port 100, the outlet port 300, the diaphragm releasing hole 510, and the electrode opening hole 2400 are made first, keeping the handle layer 970 of the middle wafer without any etching. Next, remove the whole handle layer 970 of the middle wafer 971 is removed as shown in FIG. 10F. The above procedures may alternatively be carried out at the same time if using chemical etching.

To release the valve structures 110 and 310, remove the exposed buried layer 960 and 920 of the middle and bottom wafers 971 and 931 as shown in FIG. 10G. Since the buried layer 960 is completely exposed after it is removed, the new exposed layer becomes the device layer 950 of the middle wafer 971. Next remove the thin film layer 900 between the inlet valve structure 110 and the inlet valve seat 120, and between the outlet valve structure 310 and the outlet valve seat 320. Only a very limited area which is surrounded by chemical solution at the gaps 140 and 340, the inlet valve port 100, outlet valve port 300, and the structures 150 and 350 that defined the valve structures 110 and 310, respectively, connects the thin film between the inlet valve moveable structure 110 and inlet valve seat 120, and between the outlet valve moveable structure 310 and outlet valve seat 320. Therefore, it should be very easy to remove. Once removed, the valve structures 110 and 310 are free to move as shown in FIG. 10H. In this step, wet chemical etching, accompanied by ultrasonic enhancement, is a preferred method. The buried device layer 920 of the bottom wafer 931 is finally exposed because of the electrode opening hole 2400, which can be used as an electrode for piezoelectric actuation.

The next step is to form a cavity 450 with a depth, for example, from 10 to 20 microns deep on the top wafer 900 as shown in FIG. 10I, which later will further become the chamber 400 of the micropump. The top wafer can be, for example, a glass or silicon wafer or any other appropriate material. The last step to make the micropump body is to connect the top wafer 990 having the cavity 450 with the device layer 950 of the middle wafer 971. In this connection, the cavity 400 is aligned with the inlet, the outlet, and the diaphragm 510 as best shown in FIG. 10J. Anodic bonding, fusion boding, and gluing are three possible non-limiting methods for the connection.

After the micropump body is formed, the next step is to provide a diaphragm actuation method. If choosing piezoelectric actuation, a simple method is to mount a piezoelectric plate or disc onto the diaphragm 510 with, for example, conductive glue as noted above.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

The invention claimed is:

1. A micropump device comprising:
an entirely rigid first wafer and an entirely flexible second wafer attached to the first wafer, the first and second wafers enclosing a chamber therebetween having a predetermined volume;
an entirely flexible third wafer being attached to the second wafer, each of the second and third wafers having an inlet section with an inlet valve component and an outlet section with an outlet valve component, both the inlet and outlet sections being in fluid communication with the chamber, the second and third wafers together forming a movable diaphragm which reduces the predetermined volume of the chamber when a portion of the diaphragm outside of the inlet and outlet sections is flexed for pumping a fluid out of the chamber, the second and third wafers collectively defining all components of the inlet and outlet valves,
wherein the inlet valve comprises an inlet valve flap formed in the second wafer and an inlet valve seat formed in the third wafer, the inlet valve flap being in contact with the inlet valve seat and covering an inlet aperture therein in a closed inlet state, the inlet valve flap being configured to move away from the inlet valve seat toward an open inlet state which uncovers the inlet aperture in the inlet valve seat, and wherein the outlet valve comprises an outlet valve flap formed in the third wafer and an outlet valve seat formed in the second wafer, the outlet valve flap being in contact with the outlet valve seat and covering an outlet aperture therein in a closed outlet state, the outlet valve flap being configured to move away from the outlet valve seat toward an open outlet state which uncovers the outlet aperture in the outlet valve seat.

2. The device of claim 1 wherein the first wafer is chosen from one of silicon and glass.

3. The device of claim 1 wherein each of the second and third wafers include a buried layer disposed between a device layer and a handle layer.

4. The device of claim 3 wherein the buried layer is chosen from one of silicon dioxide and germanium.

5. The device of claim 1 wherein the inlet section further comprises an inlet port.

6. The device of claim 1 wherein the inlet valve flap includes an inlet valve edge extending from the inlet valve flap toward the inlet valve seat.

7. The device of claim 1 wherein the outlet section further comprises an outlet port.

8. The device of claim 1 wherein the outlet valve flap includes an outlet valve edge extending from the outlet valve flap toward the outlet valve seat.

9. The device of claim 1 wherein the diaphragm is configured to be actuated such that the diaphragm moves away from the chamber during a first predetermined period and moves toward the chamber during a second predetermined period.

10. The device of claim 9 wherein the diaphragm is actuated by at least one of piezoelectric actuation, electromagnetic actuation, external position-fixed electromagnetic actuation, pneumatic actuation, and thermo-pneumatic actuation.

11. The device of claim 10 wherein a piezoelectric plate is attached to the diaphragm for piezoelectric actuation.

12. The device of claim 11 wherein a device layer of the third wafer is configured as a first electrode for piezoelectric actuation and the piezoelectric plate is configured as a second electrode for piezoelectric actuation.

13. The device of claim 10 wherein magnetic material is attached to the diaphragm for electromagnetic actuation with a coil disposed about a yoke operatively engaged with the magnetic material.

14. The device of claim 13 wherein the coil is connected to an AC source to provide AC current, and a changing direction of the AC current generates alternating magnetic flux causing a magnetic force on the magnetic material to change, making the diaphragm of the micropump move periodically.

* * * * *

UNITED STATES PATENT AND TRADEMARK OFFICE
CERTIFICATE OF CORRECTION

PATENT NO. : 8,475,144 B2
APPLICATION NO. : 12/239919
DATED : July 2, 2013
INVENTOR(S) : Kang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1042 days.

Signed and Sealed this
Thirtieth Day of December, 2014

Michelle K. Lee
*Deputy Director of the United States Patent and Trademark Office*